United States Patent [19]

Rehwinkel et al.

[11] Patent Number: 5,169,960
[45] Date of Patent: Dec. 8, 1992

[54] PROCESS FOR THE PRODUCTION OF E/Z MIXTURES OF 2-(BICYCLO(3.3)OCTAN-3-YLIDENE)-ACETIC ACID DERIVATIVES WITH PREDOMINANT E OR Z PORTION

[75] Inventors: Hartmut Rehwinkel; Helmut Vorbruggen, both of Berlin; Hans-Joachim Gais, Freiburg; Gerhard Schmiedl, Freiburg; Jorg Bund, Freiburg, all of Fed. Rep. of Germany

[73] Assignee: Schering Aktiengesellschaft, Berlin & Bergkamen, Fed. Rep. of Germany

[21] Appl. No.: 758,189

[22] Filed: Sep. 12, 1991

Related U.S. Application Data

[63] Continuation of Ser. No. 340,725, filed as PCT/DE88/00503, Aug. 11, 1988, published as WO89/01470, Feb. 23, 1989, abandoned.

[30] Foreign Application Priority Data

Aug. 11, 1987 [DE] Fed. Rep. of Germany ....... 3727065

[51] Int. Cl.$^5$ ................. C07D 339/06; C07D 319/06; C07D 317/08; C07F 7/04
[52] U.S. Cl. .................... 549/39; 549/375; 549/448; 556/441
[58] Field of Search ........... 549/39, 448, 375; 556/441

[56] References Cited

U.S. PATENT DOCUMENTS 4,359,581 11/1982 Skuball et al. .......... 556/441
4,810,805 3/1989 Shibasaki et al. ........ 556/441

FOREIGN PATENT DOCUMENTS 0119949 9/1984 European Pat. Off. ........... 549/448

OTHER PUBLICATIONS

Hanessian et al., Journal of Americal Chemical Society, 106, pp. 5754–5756 (1984).
Duraisamy et al., Journal of Americal Chemical Society, 105, pp. 3252–3264 (1983).

Primary Examiner—Mary C. Lee
Assistant Examiner—Joseph K. McKane
Attorney, Agent, or Firm—Millen, White, Zelano and Branigan

[57] ABSTRACT

The invention relates to a process for the production of E/Z mixtures of 2-(bicyclo[3.3.0]octan-3-ylidene)-acetic acid derivatives of Formula I,

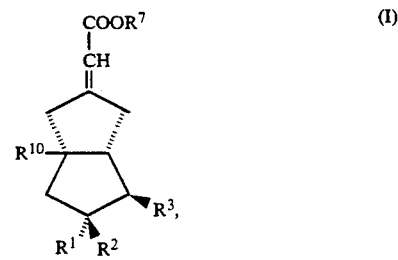

in which either the E or the Z portion predominates.

16 Claims, No Drawings

PROCESS FOR THE PRODUCTION OF E/Z MIXTURES OF 2-(BICYCLO(3.3)OCTAN-3-YLIDENE)-ACETIC ACID DERIVATIVES WITH PREDOMINANT E OR Z PORTION

This application is a continuation of application Ser. No. 07/340,725, now abandoned, filed as PCT/DE88/00503, Aug. 11, 1988, published as WO89/01470, Feb. 23, 1989.

SUMMARY OF THE INVENTION

Optically active 6alpha-carbacyclin and in particular several compounds derived from it are therapeutically very interesting as stable analogs of natural prostacyclin (PGI$_2$). [R. C. Nickolson, M. H. Town, and H. Vorbrueggen, Medicinal Research Reviews 5, 1 (1985)].

During synthesis of 6alpha-carbacyclins, if the top chain is introduced by a Wittig reaction, about 50% of the biologically potent 5E and about 50% of the biologically almost inactive 5Z analogs always result.

Asymmetrical Horner-Emmons olefinations or related reactions to generate the double bond have been described previously only by Toemoeskoezi and Janzso (Chem. Ind. 1962, 2085), which react (−)-menthylphosphonoacetate-P,P-diethylester with 4-substituted cyclohexanones. But the optical yields they obtained were very small.

Further, Bestmann and Lienert [Angew. Chem. (Applied Chemistry) 81, 751 (1969)] described a synthesis of optically active benzylidenecyclohexanes from 4-substituted cyclohexanones and the relatively difficult to access (R)-benzylidene-methylphenyl-n-propylphosphorane.

Hanessian et al. further reacted 3- and 4-substituted cyclohexanones with chiral phosphonamides for introduction of the optical activity [J. Amer. Chem. Soc. 106, 5754 (1984)].

Finally, Erdelmeier and Gais obtained, from 7,7-ethylenedioxy-bicyclo[3.3.0]octan-3-one and lithiated chiral sulfoximines, unsymmetrical olefins [Angew. Chem. 98, 912 (1986)].

Now it has been found surprisingly that, during the reaction of bicyclo[3.3.0]octan-3-one derivatives with chiral phosphonates, the corresponding 2-(bicyclo[3.3.0]octan-3-ylidene)-acetic acid derivatives result with an unexpectedly high E or Z portion.

The invention thus relates to a process for the production of E/Z mixtures of 2-(bicyclo[3.3.0]octan-3-ylidene)-acetic acid derivatives of formula I,

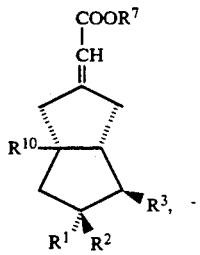
(I)

in which either the E or Z portion predominates, in which
R$^1$ means OCH$_3$, OC$_2$H$_5$,

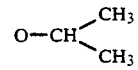

and, if R$^2$ represents hydrogen, the radical OR$^4$ with R$^4$ in the meaning of a hydrogen, trialkylsilyl, diphenylalkylsilyl, tert.-butylmethoxyphenylsilyl, trityl, tetrahydropyranyl, C$_7$-C$_{11}$ aroyl or C$_1$-C$_6$ acyl,
R$^2$ means OCH$_3$, OC$_2$H$_5$,

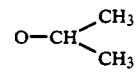

R$^1$ and R$^2$ together mean the radicals

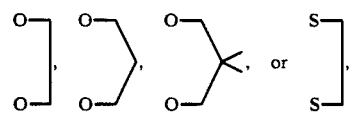

R$^3$ means hydrogen, —CH$_2$OR$^4$ with R$^4$ in the meaning given above or —A—W—D—E—R$^5$, in which
A can be a trans—CH=CH, a —CH=CBr or a —C≡C group,
W can be the radicals

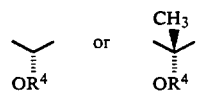

with R$^4$ in the meaning given above,
D can be a straight-chain alkylene group with 1-7 C atoms or a branched-chain alkylene group with 2-7 C atoms,
E can be a —C≡C, —CH=CR$^6$, —O—R$^5$ or —S—R$^5$ group,
R$^5$ can be an alkyl group with 1-6 C atoms,
D—E—R$^5$ can be a cycloalkyl group with 3-8 C atoms or the radical —CH$_2$—O—

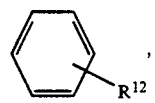

R$^6$ can be an alkyl group with 1-6 C atoms or halogen,
R$^{12}$ can be hydrogen, 4-halogen or 3-trifluoromethyl,
R$^7$ means (+)- or (−)-menthyl, (+)- or (−)-8-arylmenthyl, (+)-8-arylneomenthyl, (+)- or (−)-trans-2-arylcycloalkyl with 3-8 C atoms in the cycloalkyl and with aryl as optionally substituted phenyl, 1- or 2-naphthyl or 1-, 2- or 9-anthranyl, optionally substituted bornyl or 3-methoxy-1,3,5-estratrien-17beta-yl and
R$^{10}$ means hydrogen, methyl, ethinyl, 1-propinyl or the radical —C≡C—(CH$_2$)$_m$—R$^{11}$,
in which m represents 2-20 and
R$^{11}$ represents hydrogen, azido, amino, methylamino, benzylamino, carboxyl, methoxycarbonyl, ethoxycarbonyl, benzyloxycarbonyl, hydroxy, cyano, bromine, chlorine or iodine, which is characterized in that a bicyclo[3.3.0]octan-3-one of formula II,

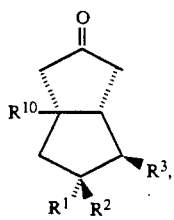

(II)

in which $R^1$, $R^2$, $R^3$ and $R^{10}$ have the meanings given above, is reacted with a chiral phosphonate of formula III

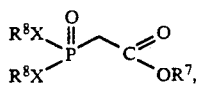

(III)

in which

X means oxygen or the radical —N($R^9$)—

$R^8$ means a straight-chain or branched alkyl radical with 1-6 C atoms, phenyl or 2,2,2-trifluoroethyl or both radicals $R^8$ together mean 1,2-cyclohexylidene and $R^9$ means hydrogen, methyl, ethyl or benzyl and $R^7$ has the meaning given above in the presence of a deprotonation agent.

If $R^4$ means trialkylsilyl or diphenylalkylsilyl, it means groups with $C_1$-$C_4$-alkyl in the alkyl part, such as, e.g., trimethylsilyl, dimethyl-tert.-butylsilyl, triethylsilyl, diphenyl-tert.-butyl- or methylsilyl.

The OH group (for $OR^4$) can be protected by protecting groups known to one skilled in the art.

$R^4$ as $C_1$-$C_6$-acyl means formyl, acetyl, propionyl, butyryl, pentanoyl, hexanoyl. Preferred are the $C_2$-$C_4$ acyls.

$R^4$ as $C_7$-$C_{11}$ aroyl means benzoyl, naphthoyl, but preferably benzoyl.

D as a staight-chain alkylene group with 1-7 C atoms is to be: methylene, ethylene, trimethylene, tetramethylene, etc. Preferred straight-chain alkylene groups D are those with 2-4 C atoms. The same holds for branched alkylene groups D with 2-7 C atoms. Suitable are the groups

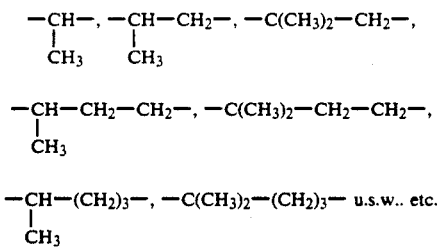

Preferred branched alkylene groups D are those with 2-4 C atoms in the chain.

$R^5$, $R^6$ and $R^8$ as alkyl groups with 1-6 C atoms are to be methyl, ethyl, n-propyl, isopropyl, n-butyl, sec.-butyl, isobutyl, tert.-butyl, pentyl, hexyl. Preferred alkyl groups $R^5$ and $R^6$ are those with 1-4 C atoms. Preferred alkyl groups $R^8$ are those with 1-3 C atoms.

D—E—$R^5$ as a cycloalkyl group with 3-8 C atoms means cyclopropyl, cyclobutyl, cyclopentyl, cyclohexyl, cycloheptyl, cyclooctyl. Groups with 4-6 C atoms are preferred. If $R^{12}$ means halogen, then chlorine and bromine are suitable. Unsubstituted phenyl is to be preferred for aryl (as substituent in radicals $R^7$).

The chiral phosphonates III (if X=O) are prepared by activation of phosphonoacetic acid-P,P-dimethyl ester (Coutrot et al., Synthesis 1978, 133) with DCC/DMAP [Neises and Steglich, Angew. Chem. (Applied Chemistry) 90, 566 (1978)] or with oxalylchloride [Miyano and Dorn. J. Org. Chem. 37, 268 (1972)] and subsequent reaction of the activated stage with the suitable optically active alcohols. Desired products III also result by heating the acids with the chiral alcohols in the presence of p-toluenesulfonic acid hydrate on the water separator. DMAP-catalyzed transesterification of trialkylphosphonoacetate with asymmetrical alcohols such as phenylmenthol also leads to the goal [Hatekeyama et al., Tetrahedron Lett. 28, 2713 (1987)].

Chiral phosphonates III with X=N-$R^9$ are obtained by reaction of methanephosphonic acid dichloride with the suitable amines in the presence of pyridine and subsequent alkylation of the resulting product with the suitable haloacetic acid esters.

According to the process according to the invention, either (E)- or (Z)-2-(bicyclo[3.3.0]octan-3-ylidene)-acetic acid derivatives can be prepared selectively in high yields. Thus expensive chromatographic separations of (1:1)-E/Z mixtures, which have been obtained according to previous processes, are simplified.

The selectively produced (E)-esters of general formula IV yield during reduction, especially with DIBAH, the corresponding (E) allyl alcohols V, which are important intermediate products for the preparation of chemically and metabolically stable 3-oxacarbacyclins such, as e.g., cicaprost and eptaprose [see W. Skuballa et al., J. Med. Chem. 29, 313 (1986)].

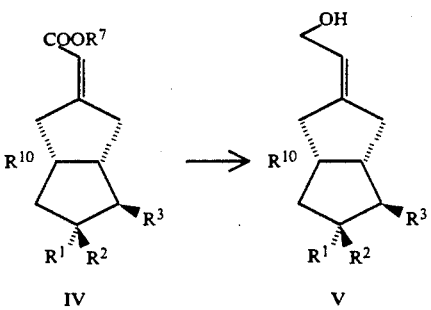

These two active ingredients lower the blood pressure and inhibit platelet aggregation. To arrive at these biologically effective compounds starting from V, after the reduction of IV to V, there is an etherification such as described, e.g., in DE-OS 3306123 [see also W. Skuballa et al., J. Med. Chem. 29, 313 (1986)].

According to more recent synthetic work, derivatives VI of allyl alcohols V, in which X represents a leaving group (X=Br, OTs, OMs, OAc), can be converted with organometallic reagents such as, e.g., Zn or Li organyls or also Grignard compounds, into the corresponding carbacyclins VII [see E. Nakamura et al., Tetrahedron Lett. 28, 337 (1987); Y. Tanigawa et al., J. Am. Chem. Soc. 99, 2361 (1977); G. Fouquet and M. Schlosser, Angew. Chem. 86, 50 (1974)].

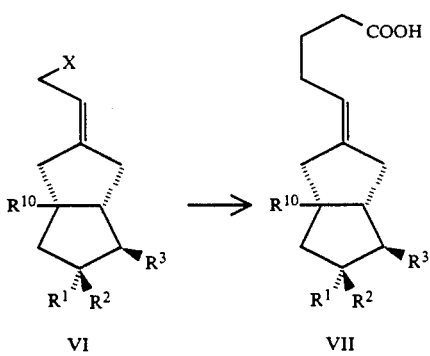

VI → VII

During the reaction of II with III, the molar ratios of the reaction partners can be varied. But it has proven to be advantageous to use an excess of the chiral phosphonate III (relative to the ketone) and not enough deprotonation agent (relative to the phosphonate III), since these measures inhibit to a great extent the formation of undesired isocarbacyclin derivatives (in which the exo-double bond has migrated in the 5-ring).

Suitable as deprotonation agents are bases known to one skilled in the art such as alkali hydrides, alkali amides, potassium-tert.-butylate, alkali salts of hexamethyldisilazane, BuLi, LDA, KDA and alkali salts of asymmetrical bases such as, e.g., (R,R)- or (S,S)-bis-(1-phenylethyl)-amine [see J. A. Marshall et al., Tetrahedron Lett. 28, 3323 (1987)]. Bases containing potassium prove to be especially advantageous for obtaining a high E/Z ratio.

The reaction of II and III is performed at temperatures of $-70°$ C. to $+44°$ C., in particular at $-40°$ C. to $+40°$ C.

As a solvent for performing the reaction, usual solvents such, as, e.g., tetrahydrofuran, diethylether, toluene, mixtures of tetrahydrofuran and toluene, 1,2-glycol dimethyl ether, diethylene glycol dimethyl ether are suitable.

To determine the E/Z ratio, the E/Z-2-(bicyclo[3.3.-0]octan-3-ylidene)-acetic acid ester is examined either directly by gas chromatography or is separated after reduction with DIBAH and subsequent reaction with N-methyl-N-(trimethylsilyl)-2,2,2-trifluoroacetamide (MSTFA) also by gas chromatography at temperatures between 100° and 300° C.

EXAMPLES

Example 1

2-[(E,Z)-(1S,5S,6R,7R)-7-hydroxy-6-(tert.-butyldiphenylsilyloxymethyl)-bicyclo[3.3.0]octan-3-ylidene]acetic acid-(+)-8-phenylmenthyl ester 306 mg (0.8 mmol) of (+)-8-phenylmenthyl phosphonoacetate-P,P-dimethyl ester is dissolved in 3 ml of anhydrous tetrahydrofuran under argon and is cooled to +5° C. After the addition of 67 mg (0.6 mmol) of potassium-tert.-butylate freshly sublimated in a vacuum, it is stirred for 10 minutes at 5° C. and, after cooling to $-35°$ C., a solution of 204 mg (0.5 mmol) of (1R,5S,6R,7R)-7-hydroxy-6-(tert.-butyldiphenylsilyloxymethyl)bicyclo[3.3.0]octan-3-one in 2 ml of anhydrous toluene is slowly instilled. After 90 hours of stirring at $-30°$ C., it is mixed with excess 0.5N HCl and the resulting mixture is taken up in 100 ml of ethyl acetate. The organic phase is washed successively with diluted HCl, saturated NaHCO$_3$ solution and brine. After drying the organic phase and evaporating the solvent, a pale oil remains that is then chromatographed on SiO$_2$ (mobile solvent hexane/ethyl acetate) and 313 mg=94% of homogeneous product is obtained. Since the E/Z ratio cannot be determined at this stage by gas chromatography, the ester is reduced to alcohol (see next example).

Example 2

2-[(E,Z)-(1S,5S,6R,7R)-7-hydroxy-6-(tert.-butyldiphenylsilyloxymethyl)-bicyclo[3.3.0]octan-3-ylidene]ethan-1-ol 313 mg (0.471 mmol) of the ester from Example 1 is dissolved in 6 ml of anhydrous toluene. At 0° under argon, 2.3 ml of a 1.25M DIBAH solution in toluene is instilled. After 1 hour of stirring at 0° C., 0.5 ml of isopropanol and then 0.5 ml of H$_2$O are instilled. After 45 minutes of stirring, taking up in ethyl acetate and drying of the organic phase, it is chromatographed on SiO$_2$ (mobile solvent hexane/ethyl acetate) and 120 mg=58% of the desired compound is isolated as oil. After silylation with MSTFA, the E/Z ratio is determined by gas chromatography (25 m quartz cap. CPSil 19CB) to be 86:10 (in addition to 4% impurities).

Example 3

2-[(E,Z)-(1S,5S,6R,7R)-7-hydroxy-6-(tert.-butyldiphenylsilyloxymethyl)-bicyclo[3.3.0]octan-3-ylidene]acetic acid-(−)-8-phenylmenthyl ester Molar amounts, performance and working up as described in example 1. Instead of the (+)-8-phenylmenthyl phosphonoacetate-P,P-dimethyl ester, the enantiomer (−)-8-phenylmenthyl phosphonoacetate-P,P-dimethyl ester is used. Chromatography on SiO$_2$ (mobile solvent hexane/ethyl acetate) yields 322 mg=97% of the desired compound, which is reduced to determine the E/Z ratio (see next example).

Example 4

2-[(E,Z)-(1S,5S,6R,7R)-7-hydroxy-6-(tert.-butyldiphenylsilyloxymethyl)-bicyclo[3.3.0]octan-3-ylidene]-ethan-1-ol Performance of the reduction using 322 mg (0.484 mmol) of the ester from Example 3. Molar ratios and conditions correspond to those in Example 2. After chromatography on SiO$_2$ (mobile solvent hexane/ethyl acetate), 138 mg=65% of colorless oil remains. After silylation of the free hydroxyl groups with MSTFA, the E/Z ratio is determined by gas chromatography to be 8:88 (in addition to 4% impurities) (25 m quartz cap. CP-Sil 19 CB).

Example 5

2-{(E,Z)-(1S,5S,6S,7R)-7-(tert.-butyldimethylsilyloxy)-6-[(3S,4S)-3-(tert.-butyldimethylsilyloxy)-4-methyl-nona-1,6-diinyl]-bicyclo[3.3.0]octan-3-ylidene}-acetic acid-(+)-8-phenylmenthyl ester 306 mg (0.8 mmol) of (+)-8-phenylmenthyl phosphonoacetate-P,P-dimethyl ester is reacted with 258 mg (0.5 mmol) of (1R,5S,6S,7R)-7-(tert.-butyldimethylsilyloxy)-6-[(3S,4S)-3-(tert.-butyldimethylsilyloxy)-6-[(3S,4S)-3-(tert.-butyldimethylsilyloxy)-4-methyl-nona-1,6-diinyl]bicyclo[3.3.0]octan-3-one as described in Example 1. It is stirred for 87 hours at $-30°$ C. After working up and chromatographing on SiO$_2$ (mobile solvent hexane/ethyl acetate), 370 mg=95% of the desired compound remains as an oil.

Example 6

2-{(E,Z)-(1S,5S,6S,7R)-7-(tert.-butyldimethylsilyloxy)-6-[(3S,4S)-3-(tert.-butyldimethylsilyloxy)-4-methyl-nona-1,6-diinyl]-bicyclo[3.3.0]octan-3-ylidene}-ethan-1-ol 335 mg (0.433 mmol) of the ester from Example 5 is reduced as described in Example 2 with 1.25 ml of a 1.2M solution of DIBAH in toluene. Working up and chromatographing on $SiO_2$ (mobile solvent hexane/ethyl acetate) yields 199 mg=84% of a colorless oil.

After silylation of the primary hydroxyl group with MSTFA, the E/Z ratio is determined by gas chromatography to be 80:20 (25 m CP Sil 8 CB).

Example 7

2-{(E,Z)-(1S,5S,6S,7R)-7-(tert.-butyldimethylsilyloxy)-6-[(3S,4S)-3-(tert.-butyldimethylsilyloxy)-4-methyl-nona-1,6-diinyl]-bicyclo[3.3.0]octan-3-ylidene}-acetic acid-(−)-8-phenylmenthyl ester Amounts, test performance and duration as described in Example 5. Instead of the (+)-8-phenylmenthyl phosphonoacetate-P,P-dimethyl ester, here the (−)-enantiomer is used. After working up and chromatographing on $SiO_2$ (mobile solvent hexane/ethyl acetate) 354 mg=91% of the desired compound remains as oil. Since the substance cannot be tested by gas chromatography, the ester is reduced (see Example 8).

Example 8

2-{(E,Z)-(1S,5S,6S,7R)-7-(tert.-butyldimethylsilyloxy)-6-[(3S,4S)-3-(tert.-butyldimethylsilyloxy)-4-methyl-nona-1,6-diinyl]-bicyclo[3.3.0]octan-3-ylidene}-ethan-1-ol Test performance and working up as described in Example 6. 316 mg (0.408 mmol) of the ester from Example 7 and 1.25 ml of a 1.2M DIBAH solution in toluene are used. After chromatography on $SiO_2$ (mobile solvent hexane/ethyl acetate), 168 mg=75% remains.

Gas chromatography under conditions as in Example 6 yields an E/Z ratio of 20:78 (in addition to 2% impurities).

Example 9

2-[(E,Z)-(1S,5S,6R,7R)-7-hydroxy-6-(tert.-butyldimethylsilyloxymethyl)-bicyclo[3.3.0]octan-3-ylidene]acetic acid-(+)-8-phenylmenthyl ester 306 mg (0.8 mmol) of (+)-8-phenylmenthyl phosphonoacetate-P,P-dimethyl ester is reacted as described in Example 1 with 142 mg (0.5 mmol) of (1R,5S,6R,7R)-7-hydroxy-6-(tert.-butyldimethylsilyloxymethyl)-bicyclo[3.3.0]octan-3-one. 115 hours at −30° C. Working up and chromatographing (mobile solvent hexane/ethyl acetate) as usual. 190 mg=70% of the desired compound remains. The E/Z ratio, after being determined by gas chromatography (25 m CP Sil 8 CB, silylation with MSTFA), is 91:4 (5% impurities).

Example 10

2-[(E,Z)-(1S,5S,6R,7R)-7-hydroxy-6-(tert.-butyldimethylsilyloxymethyl)-bicyclo[3.3.0]octan-3-ylidene]acetic acid-(−)-8-phenylmenthyl ester 306 mg (0.8 mmol) of (−)-8-phenylmenthyl phosphonoacetate-P,P-dimethyl ester is reacted as described with 142 mg (0.5 mmol) of (1R,5S,6R,7R)-7-hydroxy-6-(tert.butyldimethylsilyloxymethyl)-bicyclo[3.3.0]octan-3-one. 115 hours at −30° C. As usual, it is worked up and chromatographed (mobile solvent hexane/ethyl acetate). 194 mg=72% of a uniform product is obtained, whose E/Z ratio is 4:94 (2% impurities) after gas chromatography (conditions, see Example 9).

Example 11

2-[(E,Z)-(1S,5S,6R,7R)-7-(tert.-butyldimethylsilyloxy)-6-(tert.-butyldimethylsilyloxymethyl)-bicyclo[3.3.0]octan-3-ylidene]acetic acid-(+)-8-phenylmenthyl ester 306 mg (0.8 mmol) of (+)-8-phenylmenthyl phosphonoacetate-P,P-dimethyl ester is reacted with 199 mg (0.5 mmol) of (1R,5S,6R,7R)-7-(tert.-butyldimethylsilyloxy)-6-(tert.-butyldimethylsilyloxymethyl)-bicyclo[3.3.0]octane-3-one under the conditions as described in Example 1. 94 hours of stirring at −25° C. After working up and chromatographing as described, 310 mg=94% of the desired compound remains. According to gas chromatography (25 m CP Sil 8 CB), the E/Z ratio is 78:22.

Example 12

2[-(E,Z)-(1S,5S,6R,7R)-7-(tert.-butyldimethylsilyloxy)-6-(tert.-butyldimethylsilyloxymethyl)-bicyclo[3.3.0]octan-3-ylidene]-acetic acid-(−)-8-phenylmenthyl ester.

306 mg (0.8 mmol) of (−)-8-phenylmenthyl phosphonoacetate-P,P-dimethyl ester is reacted as described with 199 mg (0.5 mmol) of (1R,5S,6R,7R)-7-(tert.-butyldimethylsilyloxy)-6-(tert.-butyldimethylsilyloxymethyl)-bicyclo[3.3.0]octan-3-one. 115 hours of stirring at −30° C. After working up and chromatography, 299 mg=91% of the desired substance is obtained. Gas chromatography (25 m CP Sil 8 CB) shows an E/Z ration of 15:85.

Example 13

2-[(E,Z)-(1S,5S,6R,7R)-7-(tert.-butyldimethylsilyloxy)-6-(tert.-butyldimethylsilyloxymethyl)-bicyclo[3.3.0]octan-3-ylidene]acetic acid-(−)-trans-2-phenyl-cyclohexyl ester 261 mg (0.8 mmol) of -(−)-trans-2-phenylcyclohexyl-phosphonoacetate-P,P-dimethyl ester is reacted as described in Example 1 with 199 mg (0.5 mmol) of (1R,5S,6R,7R)-7-(tert.-butyldimethylsilyloxy)-6-(tert.-butyldimethylsilyloxymethyl)-bicyclo[3.3.0]octan-3-one. After 87 hours of stirring at −30° C., working up and chromatographing, 280 mg=93% of the desired compound remains as a pale oil. Separation by gas chromatography yields an E/Z ratio of 77:23 (25 m CP Sil 8 CB).

We claim:
1. A process for the production of E/Z mixtures of 2-(bicyclo[3.3.0]octan-3-ylidine)-acetic acid derivatives of formula I, in which either the E or Z portion predominates,

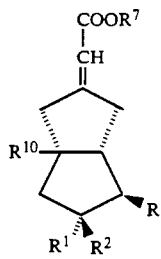

(I)

wherein
R$^1$ is OCH$_3$, OC$_2$H$_5$, O—CH(CH$_3$)$_2$ and, if R$^2$ is H, R$^1$ can be OR$^4$ with R$^4$ being H, trialkylsilyl, diphenylalkylsilyl, tert.-butylmethoxyphenylsilyl, trityl, tetrahydropyranyl, C$_7$-C$_{11}$ aroyl or C$_1$-C$_6$ acyl;

R$^2$ is H, OCH$_3$, OC$_2$H$_5$, or O—CH(CH$_3$)$_2$;

R$^1$ and R$^2$, together, can also be

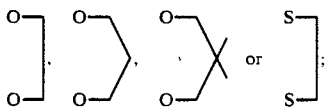

R$^3$ is H, —CH$_2$OR$^4$ with R$^4$ having the meaning given above, or —A—W—D—E—R$^5$;

A is trans—CH=CH, —CH=CBr or —C≡C;

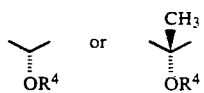

W is with R$^4$ having the meaning given above;

D is a straight-chain alkylene with 1-7 C atoms or a branched-chain alkylene with 2-7 C atoms;

E is a —C≡C, —CH=CR$^6$, —O—R$^5$ or —S—R$^5$;

R$^5$ is an alkyl with 1-6 C atoms;

D—E—R$^5$ can also be a cycloalkyl with 3-8 C atoms or

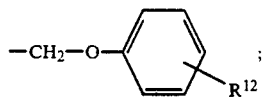

R$^6$ is halogen or an alkyl with 1-6 C atoms;

R$^{12}$ is H, 4-halogen or 3-trifluoromethyl;

R$^7$ is (+)- or (−)-menthyl, (+)- or (−)-8-arylmenthyl, (+)-8-arylneomenthyl, (+)- or (−)-trans-2-arylcycloalkyl with 3-8 C atoms in the cycloalkyl group and the aryl group being unsubstituted phenyl, substituted phenyl, 1- or 2-naphthyl or 1-, 2- or 9-anthranyl, unsubstituted bornyl, substituted bornyl, or 3-methoxy-1,3,5-estratrien-17beta-yl;

R$^{10}$ is H, methyl, ethinyl, 1-propinyl or —C≡C—(CH$_2$)$_m$—R$^{11}$;

m is 2-20; and

R$^{11}$ is H, azido, amino, methylamino, benzylamino, carboxyl, methoxycarbonyl, ethoxycarbonyl, benzyloxycarbonyl, hydroxy, cyano, bromine, chlorine or iodine;

said process comprising reacting, in the presence of a deprotonation agent, a bicyclo octan-3-one of formula II,

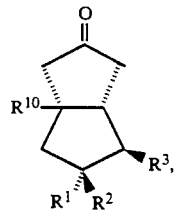

(II)

in which R$^1$, R$^2$, R$^3$ and R$^{10}$ have the meanings given above, with a chiral phosphonate of formula III

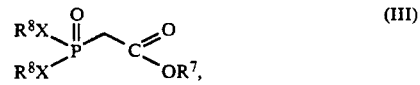

(III)

wherein
X is oxygen or —N(R$^9$)—;

R$^8$ is a straight-chain or branched alkyl with 1-6 C atoms, phenyl or 2,2,2-trifluoroethyl, or both R$^8$ radicals together are 1,2-cyclohexylidene;

R$^9$ is H, methyl, ethyl or benzyl; and

R$^7$ has the meaning given above.

2. A process according to claim 1, wherein R$^4$ is tri-C$_{1-4}$-alkylsilyl or diphenyl-C$_{1-4}$-alkylsilyl.

3. A process according to claim 1, wherein R$^4$ is a C$_{2-4}$-acyl.

4. A process according to claim 1, wherein R$^4$ is benzoyl or naphthoyl.

5. A process according to claim 1, wherein D is a C$_{2-4}$-straight-chain alkylene or C$_{2-4}$-branched-chain alkylene.

6. A process according to claim 1, wherein R$^5$ and R$^6$ are each, independently, a C$_{1-4}$-alkyl.

7. A process according to claim 1, wherein R$^8$ is a C$_{1-3}$-alkyl.

8. A process according to claim 1, wherein D—E—R$^5$ is a C$_{4-6}$-cycloalkyl.

9. A process according to claim 1, wherein R$^{12}$ is Cl or Br in the 4-position.

10. A process according to claim 1, wherein the aryl portion of the R$^7$ radical is unsubstituted phenyl.

11. A process according to claim 1, wherein the reaction is performed with an excess of the chiral phosphonate of formula III.

12. A process according to claim 1, wherein the reaction is formed with a deficient amount of deprotonation agent with respect to the chiral phosphonate of formula III.

13. A process according to claim 11, wherein the reaction is formed with a deficient amount of deprotonation agent with respect to the chiral phosphonate of formula III.

14. A process according to claim 1, wherein said deprotonation agent is a potassium containing base.

15. A process according to claim 1, wherein the reaction is performed at a temperature of about −70° to +44° C.

16. A process according to claim 1, wherein the reaction is performed in a solvent selected from the group comprising tetrahydrofuran, diethylether, toluene, mixtures of tetrahydrofuran and toluene, 1,2-glycol dimethylether or diethyleneglycol dimethylether.

* * * * *